United States Patent [19]
Bieringer et al.

[11] Patent Number: 6,124,240
[45] Date of Patent: *Sep. 26, 2000

[54] COMBINATIONS OF SULFONYLUREA HERBICIDES AND SAFENERS

[75] Inventors: Hermann Bieringer, Eppstein; Erwin Hacker, Hochheim; Heinz Kehne; Lothar Willms, both of Hofheim, all of Germany

[73] Assignee: Hoechst AgrEvo GmbH, Berlin, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/932,717

[22] Filed: Sep. 17, 1997

[30] Foreign Application Priority Data

Sep. 19, 1996 [DE] Germany ............ 196 38 233

[51] Int. Cl.⁷ ............ A01N 25/32; A01N 43/54
[52] U.S. Cl. ............ 504/105; 504/106
[58] Field of Search ............ 504/105, 106

[56] References Cited

U.S. PATENT DOCUMENTS

| | | | |
|---|---|---|---|
| 4,639,266 | 1/1987 | Heubach et al. | 71/92 |
| 4,668,276 | 5/1987 | Handte et al. | 71/88 |
| 4,881,966 | 11/1989 | Nyffeier et al. | 71/94 |
| 4,891,057 | 1/1990 | Sohn et al. | 71/72 |
| 4,902,340 | 2/1990 | Hubele | 71/94 |
| 5,054,107 | 10/1991 | Batchelder | 392/483 |
| 5,314,863 | 5/1994 | Löher et al. | 504/100 |
| 5,371,060 | 12/1994 | Glock et al. | 504/106 |
| 5,393,734 | 2/1995 | Andrea et al. | 504/215 |
| 5,571,772 | 11/1996 | Willms et al. | 504/106 |

FOREIGN PATENT DOCUMENTS

| | | |
|---|---|---|
| 34951/89 | 5/1989 | Australia . |
| 2058276 | 12/1991 | Canada . |
| 2101684 | 7/1993 | Canada . |
| 0 086 750 | 8/1983 | European Pat. Off. . |
| 0 094 349 | 11/1983 | European Pat. Off. . |
| 0 174 562 | 3/1986 | European Pat. Off. . |
| 0 191 736 | 8/1986 | European Pat. Off. . |
| 0 333 131 | 9/1989 | European Pat. Off. . |
| 0 346 620 | 12/1989 | European Pat. Off. . |
| 0 154 153 | 8/1990 | European Pat. Off. . |
| 0 269 806 | 2/1991 | European Pat. Off. . |
| 0 492 366 | 7/1992 | European Pat. Off. . |
| 0 502 740 | 9/1992 | European Pat. Off. . |
| 0524394 | 1/1993 | European Pat. Off. . |
| 0558448 | 9/1993 | European Pat. Off. . |
| 0 582 198 | 2/1994 | European Pat. Off. . |
| 1542872 | 7/1970 | Germany . |
| 3539476 | 5/1987 | Germany . |
| 4 421730 | 11/1995 | Germany . |
| 89/1960 | 3/1989 | South Africa . |
| 90/9591 | 11/1990 | South Africa . |
| 94/7120 | 6/1995 | South Africa . |
| WO 91/07874 | 6/1991 | WIPO . |
| WO 91/08202 | 6/1991 | WIPO . |
| WO 94/03064 | 2/1994 | WIPO . |
| WO 94/26716 | 11/1994 | WIPO . |
| WO 95/07897 | 3/1995 | WIPO . |
| WO 95/08919 | 4/1995 | WIPO . |
| WO 95/30639 | 11/1995 | WIPO . |
| WO 97/18712 | 5/1997 | WIPO . |

OTHER PUBLICATIONS

Laboratoire de Chimie de l'E.N.S., 24 rue Lhomond, 7523, Paris, Cedex 05, publication entitled "Bulletin de la Societe Chimique de France 1986, No. 3". pp. 423–428.

Laboratoire de Chimie de l'E.N.S., 24 rue Lhomond, 7523, Paris, Cedex 05, publication entitled "Bulletin de la Societe Chimique de France 1987, No. 5". pp. 861–866.

(List continued on next page.)

*Primary Examiner*—S. Mark Clardy
*Attorney, Agent, or Firm*—Frommer Lawrence & Haug LLP

[57] ABSTRACT

Phytotoxic side effects of the herbicide of the formula (A1) (flupyrsulfuron) or herbicidal salts thereof

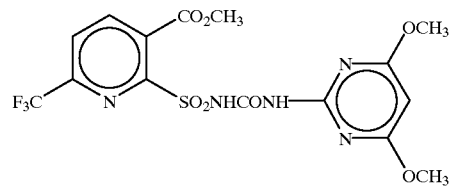

(A1)

on crops, preferably cereals and maize, can be prevented by combining the herbicides with safeners (B) from the group a) compounds of the formulae (B1) and (B2),

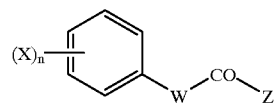

(B1)

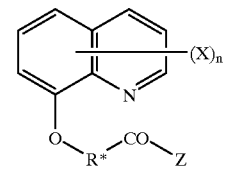

(B2)

in which

W is a divalent heterocyclic radical from the group of the partially unsaturated or heteroaromatic five-membered heterocycles having 1 to 3 hetero ring atoms of the type N and O, at least one nitrogen atom and at the most one oxygen atom being present in the ring, and X, n, Z, R*, and W are as defined in claim 1, and/or b) compounds of the group of the hormonal growth regulators (auxins).

17 Claims, No Drawings

OTHER PUBLICATIONS

Tetrahedron Letters, vol. 34, No. 43, pp. 6903–6906 by Clemenceau et al.
The Journal of Organic Chemistry, vol. 33, No. 1, Jan. 1968, pp. 286–291 by Drakesmith et al.
J. Org. Chem., 1990, 55, pp. 4782–4784 by Welch et al.
Chemical Abstract, vol. 124, No. 5, 1996, No. 124: 55063g.
J. Chem. Soc., 1968, p. 1232–1235 by Bergman et al.

C.R. Acad. Sc. Paris, t, 270 (Jan. 26, 1970) by Charlotte Francesch.

Bulletin de la Societe Chimique de France 1967, No. 5. p. 1569–1571.

Bulletin de la Societe Chimique de France 1973, No. 4. p. 1281–1285.

COMBINATIONS OF SULFONYLUREA HERBICIDES AND SAFENERS

The invention relates to the technical field of crop protection agents, in particular active compound/antidote combinations (=active compound/safener combinations) which are outstandingly suitable for use against competing harmful plants in crops of useful plants.

Some of the more recent herbicidally active compounds have very good application properties and can be employed at very low application rates against a wide range of grass-like and broad-leaved weeds.

However, many of the highly active compounds are not fully compatible with (i.e. not selective enough in) some important crops, such as maize, rice or cereals, thus considerably restricting their use. In some crops they can therefore not be employed at all or only at application rates so low that the desired broad herbicidal activity against harmful plants is not ensured. Specifically, the herbicide of the formula (A1) defined further below and salts thereof cannot be employed entirely selectively against harmful plants in maize, rice, cereals or some other crops.

Some of our recent experimental work has shown that crops, such as maize, rice, wheat, barley and others, can surprisingly be protected against undesirable damage by the herbicides mentioned when they are applied together with certain compounds which act as herbicide antidote or safener.

The invention, accordingly, provides herbicide/safener combinations, for example in the form of herbicidal compositions, comprising A) as herbicidally active compound a pyridylsulfonylurea of the formula (A1) which is little or only partially selective in cereals or a salt thereof

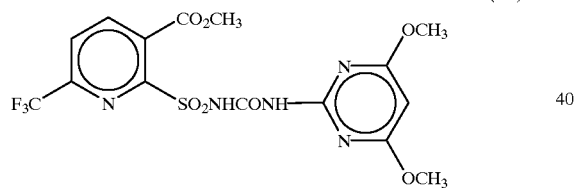
(A1)

and
B) one or more safeners
  a) from the group of the compounds of the formulae (B1) and (B2),

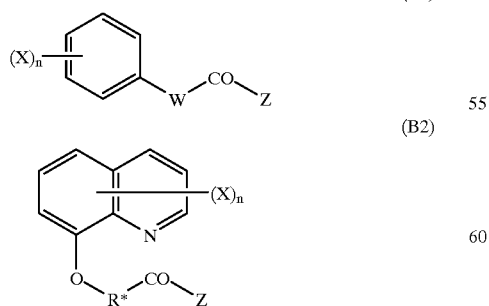
(B1)
(B2)

in which
X is hydrogen, halogen, $(C_1-C_4)$alkyl, $(C_1-C_4)$alkoxy, nitro or $(C_1-C_4)$haloalkyl, n is an integer from 1 to 5, preferably 1 to 3, Z is $OR^1$, $SR^1$ or $NR^1R^2$ or is a saturated or unsaturated 3- to 7-membered heterocycle having at least one nitrogen atom and up to 3 hetero atoms which is linked to the carbonyl group in (B1) or (B2) via the nitrogen atom and which is unsubstituted or substituted by radicals from the group consisting of $(C_1-C_4)$alkyl, $(C_1-C_4)$alkoxy or phenyl with or without substitution, preferably a radical of the formula $OR^1$, $NHR^2$ or $N(CH_3)_2$, in particular of the formula $OR^1$, $R^*$ is a ($C_1$ or $C_2$)-alkanediyl chain which is unsubstituted or substituted by one or two $(C_1-C_4)$alkyl radicals or by [$(C_1-C_3)$-alkoxy]carbonyl, $R^1$ is hydrogen or an unsubstituted or substituted aliphatic hydrocarbon radical, preferably having a total of 1 to 18 carbon atoms, $R^2$ is hydrogen, $(C_1-C_6)$alkyl, $(C_1-C_6)$alkoxy or phenyl with or without substitution, W is a divalent heterocyclic radical from the group of the partially unsaturated or heteroaromatic five-membered heterocycles having 1 to 3 hetero ring atoms of the type N and O, at least one nitrogen atom and at the most one oxygen atom being present in the ring, preferably a radical from the group of the radicals of the formulae (W1) to (W4),

(W1)

(W2)

(W3)

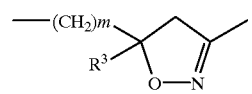
(W4)

$R^3$ is hydrogen, $(C_1-C_8)$alkyl, $(C_1-C_8)$haloalkyl, $(C_3-C_{12})$cycloalkyl or phenyl with or without substitution, $R^4$ is hydrogen, $(C_1-C_8)$alkyl, $(C_1-C_8)$haloalkyl, $(C_1-C_4)$alkoxy$(C_1-C_4)$alkyl, $(C_1-C_6)$hydroxyalkyl, $(C_3-C_{12})$cycloalkyl or tri-$(C_1-C_4)$-alkylsilyl and m is 0 or 1, or b) from the group of the hormonal acting growth regulators (auxins), preferably the compounds of the formulae (B3)–(B6) or salts or esters thereof,

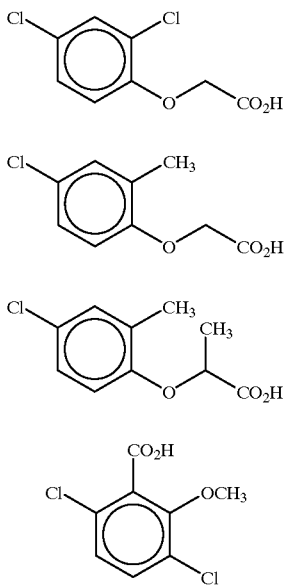

or c) from a combination of the safeners listed under a) and b).

In addition to their action as safeners in combination with herbicides of the formula (A), the abovementioned compounds of the formulae (B1) to (B6) have the common feature that structurally they belong to the carboxylic acid derivatives of the formula

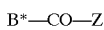

wherein

Z is as defined above and

B is a (hetero)aromatic radical which is attached via a direct bond or an aliphatic or heterocyclic bridge member.

Unless specifically defined otherwise, the following definitions apply to the radicals in the formulae (B1) and (B2) and the formulae below:

The radicals alkyl, alkoxy, haloalkyl, haloalkoxy, alkylamino and alkylthio and the corresponding unsaturated and/or substituted radicals can in each case be straight-chain or branched in the carbon skeleton. Unless specifically mentioned, the lower carbon skeletons, for example those having 1 to 6 carbon atoms or, in the case of unsaturated groups, 2 to 6 carbon atoms, are preferred for these radicals. Alkyl radicals, also in the composite meanings such as alkoxy, haloalkyl and the like, are, for example, methyl, ethyl, n- or i-propyl, n-, i-, t- or 2-butyl, pentyl radicals, hexyl radicals such as n-hexyl, i-hexyl and 1,3-dimethylbutyl, heptyl radicals, such as n-heptyl, 1-methylethyl and 1,4-dimethylpentyl; alkenyl and alkynyl have the meanings of the unsaturated radicals which are possible and which correspond to the alkyl radicals; cycloalkyl is a cycloaliphatic hydrocarbon radical such as cyclopropyl, cyclobutyl, cyclopentyl or cyclohexyl and the like; alkenyl is, for example, allyl, 1-methylprop-2en-1-yl, 2-methylprop-2-en-1-yl, but-2-en-1-yl, but-3-en-1-yl, 1-methylbut-3-en-1-yl and 1-methylbut-2-en-1-yl; cycloalkenyl is, for example, cyclopentenyl and cyclohexenyl; alkynyl is, for example, propargyl, but-2-yn-1-yl, but-3-yn-1-yl or 1-methylbut-3-yn-1-yl. "$(C_1-C_4)$Alkyl" is the short notation for alkyl having 1 to 4 carbon atoms; the same applies analogously to other general radical definitions where the ranges for the possible number of carbon atoms is stated in brackets.

Alkenyl in the form "$(C_3-C_4)$alkenyl" or "$(C_3-C_6)$ alkenyl" is preferably an alkenyl radical having 3 to 4 and 3 to 6 carbon atoms, respectively, where the double bond is not located on the carbon atom attached to the remaining moiety of the compound (I) ("yl" position). The same applies analogously to $(C_3-C_4)$alkynyl and the like.

Halogen is, for example, fluorine, chlorine, bromine or iodine. Haloalkyl, haloalkenyl and haloalkynyl are alkyl, alkenyl and alkynyl, respectively, which are fully or partially substituted by halogen, preferably by fluorine, chlorine and/or bromine, in particular by fluorine or chlorine, such as $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; the same applies analogously to haloalkenyl and other halogen-substituted radicals.

A hydrocarbon radical is a straight-chain, branched or cyclic and unsaturated or saturated aliphatic or aromatic hydrocarbon radical, such as alkyl, alkenyl, alkynyl, cycloalkyl, cycloalkenyl or aryl; preferably a hydrocarbon radical is alkyl, alkenyl or alkynyl having up to 12 carbon atoms or cycloalkyl having 3, 4, 5, 6, 7 or 8 ring atoms or phenyl; the same applies analogously to a hydrocarbon radical in a hydrocarbonoxy radical.

Aryl is a monocyclic, carbocyclic aromatic ring which includes, in the case that it is substituted, also a bi- or polycyclic aromatic system containing at least one aromatic ring and optionally further aromatic rings or partially unsaturated or saturated rings; aryl is, for example, phenyl, naphthyl, tetrahydronaphthyl, indenyl, indanyl, pentalenyl, fluorenyl and the like, preferably phenyl;

heteroaryl or a heteroaromatic radical is a mono-, bi- or polycyclic aromatic system in which at least 1 ring contains one or more hetero atoms, for example pyridyl, pyrimidinyl, pyridazinyl, pyrazinyl, thienyl, thiazolyl, oxazolyl, isoxazolyl, furyl, pyrrolyl, pyrazolyl and imidazolyl. In the case of substitution, bicyclic or polycyclic aromatic or benzon fused com pounds or compounds fused with cycloaliphatic rings, for example quinolinyl, benzoxazolyl and the like, are also particularly included. Heteroaryl also includes a heteroaromatic ring which is preferably 5- or 6-membered and contains 1, 2 or 3 hetero ring atoms, in particular from the group consisting of N, O and S.

A heterocyclic radical (heterocyclyl) or ring (heterocyclus) can be saturated, unsaturated or heteroaromatic (heteroaryl); it contains one or more hetero ring atoms, preferably from the group consisting of N, O and S; it is preferably a non-aromatic ring having 3 to ring atoms and 1 to 3 hetero ring atoms from the group consisting of N, O and S or it is a heteroaromatic ring having 5 or 6 ring atoms and contains 1, 2 or 3 hetero ring atoms from the group consisting of N, O and S. The radical can be, for example, a heteroaromatic radical or ring as defined above, or it is a partially hydrogenated radical such as oxiranyl, pyrrolidyl, piperidyl, piperazinyl, dioxolanyl, morpholinyl, tetrahydrofuryl. Substituents which are suitable for a substituted heterocyclic radical are the substituents mentioned further below, and additionally also oxo. The oxo group can also be present on the hetero ring atoms, which can exist at various oxidation levels, for example in the case of N and S.

Substituted radicals, such as substituted hydrocarbon radicals, for example substituted alkyl, alkenyl, alkynyl, aryl and phenyl, or substituted heterocyclyl or heteroaryl, are, for example, a substituted radical derived from the unsubstituted skeleton, the substituents being, for example, one or more, preferably 1, 2 or 3, radicals from the group consisting of halogen, alkoxy, haloalkoxy, alkylthio, hydroxyl, amino, nitro, carboxy, cyano, azido, alkoxycarbonyl, alkylcarbonyl, formyl, carbamoyl, mono- and dialkylaminocarbonyl, substituted amino, such as acylamino or mono- and dialkylamino, and alkylsulfinyl, haloalkylsulfinyl, alkylsulfonyl, haloalkylsulfonyl and, in the case of cyclic radicals, also alkyl and haloalkyl, and unsaturated aliphatic radicals which correspond to the abovementioned saturated hydrocarbon-containing radicals, such as alkenyl, alkynyl, alkenyloxy, alkynyloxy and the like. Preferred among the radicals having carbon atoms are those having 1 to 4 carbon atoms, in particular 1 or 2 carbon atoms. Preferred substituents are generally selected from the group consisting of halogen, for example fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Especially preferred are the substituents methyl, methoxy and chlorine.

Unsubstituted or substituted phenyl is preferably phenyl which is unsubstituted or mono- or polysubstituted, preferably up to trisubstituted, by identical or different radicals from the group consisting of halogen, $(C_1-C_4)$alkyl, $(C_1-C_4)$alkoxy, $(C_1-C_4)$haloalkyl, $(C_1-C_4)$haloalkoxy und nitro, for example o-, m- and p-tolyl, dimethylphenyl radicals, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

Mono- or disubstituted amino is a chemically stable radical selected from the group consisting of the substituted amino radicals which are N-substituted, for example, by one or two identical or different radicals selected from the group consisting of alkyl, alkoxy, acyl and aryl; preferably monoalkylamino, dialkylamino, acylamino, arylamino, N-alkyl-N-arylamino and N-heterocycles; preferred are alkyl radicals having 1 to 4 carbon atoms; aryl is preferably phenyl or substituted phenyl; acyl is defined as indicated further below and is preferably $(C_1-C_4)$alkanoyl. The same applies analogously to substituted hydroxylamino or hydrazino.

An acyl radical is the radical of an organic acid, for example the radical of a carboxylic acid and radicals of acids derived therefrom, such as thiocarboxylic acid, iminocarboxylic acids with or without N-substitution, or the radical of carbonic monoesters, carbamic acid with or without N-substitution, sulfonic acids, sulfinic acids, phosphonic acids, phosphinic acids. Acyl is, for example, formyl, alkylcarbonyl such as $[(C_1-C_4)$alkyl]carbonyl, phenylcarbonyl where the phenyl ring may be substituted, for example as shown above for phenyl, or alkyloxycarbonyl, phenyloxycarbonyl, benzyloxycarbonyl, alkylsulfonyl, alkylsulfinyl, N-alkyl-1-iminoalkyl and other radicals of organic acids.

The formulae (B1), (B2) and (B5) also embrace all stereoisomers having the same topological attachment of atoms, and mixtures thereof. Such compounds contain one or more asymmetric carbon atoms or else double bonds which are not specifically indicated in the formulae. The stereoisomers which are possible and which are defined by their specific spatial form, such as enantiomers, diastereomers, Z isomers and E isomers, can be obtained from stereoisomer mixtures by customary methods, or else be prepared by stereoselective reactions in combination with the use of stereochemically pure starting materials.

The formulae also embrace tautomers of the indicated compounds, as far as they are formed by proton migration and as far as they are chemically stable tautomers.

The compounds of the formulae (A1) and (B3) to (B6), and also (B1) and (B2) if they contain free carboxyl groups or other groups having acidic hydrogen atoms, can form salts where the hydrogen of the —$SO_2$—NH group, the $CO_2H$ group or another acidic group is replaced by an agriculturally suitable cation. These salts are, for example, metal salts, in particular alkali metal salts or alkaline earth metal salts, especially sodium salts and potassium salts, or else ammonium salts or salts with organic amines.

The compounds of the formula (B1) are known from EP-A-333 131 (ZA89/1960), EP-A-269 806 (U.S. Pat. No. 4,891,057), EP-A-346 620 (AU-A-89/34951), EP-A-174 562, EP-A-346 620 and the international patent applications PCT/EP 90/01966 (WO-91/08202) and PCT/EP 90/02020 (WO-91/07874) and the German patent application P 43 31 448.1 (WO 95/07897 or ZA 94/7120) and the literature cited therein, or they can be prepared by or similarly to the processes described therein. The compounds of the formula (B2) are known from EP-A-86 750, EP-A-94 349 (U.S. Pat. No. 4,902,340), EP-A-191 736 (U.S. Pat. No. 4,881,966) and EP-A-492 366 and the literature cited therein, or they can be prepared by or similarly to the processes described therein. Furthermore, some compounds are described in EP-A-0582198.

The compounds of the formulae (B3) to (B6) are pesticides which are also known under the names 2,4-D (B3), MCPA (B4), mecoprop (B5) and dicamba (B6); see, for example, C. Tomlin (Ed.), The Pesticide Manual, 10th edition, The British Crop Protection Council and the Royal Society of Chemistry, 1994. They belong to the hormone-like acting growth regulators which include further compounds suitable for use as safeners; cf. substituted phenoxycarboxylic acids (for example EP-A-154153, U.S. Pat. No. 4668276), inter alia.

Suitable for use as herbicidally active compounds according to the invention are the compound of the formula (A1) and salts thereof (hereinbelow also called "active compounds (A)") which cannot or cannot optimally be used on their own in cereals, in particular barley, maize and/or rice, because they cause too much damage to the crops.

The compound of the formula (A1) and the sodium salt thereof are known from EPA-502740 (company code: DPX-KE 459 for the sodium salt).

Of particular interest are herbicide/safener combinations according to the invention where in the safeners (B1) or (B2) $R^1$ is hydrogen, $(C_1-C_{18})$alkyl, $(C_3-C_{12})$cycloalkyl, $(C_2-C_8)$alkenyl or $(C_2-C_8)$alkynyl where the abovementioned carbon-containing radicals are unsubstituted or mono- or polysubstituted, preferably up to trisubstituted, by identical or different radicals from the group consisting of halogen, hydroxyl, $(C_1-C_8)$alkoxy, $(C_1-C_8)$alkylmercapto, $(C_2-C_8)$alkenylmercapto, $(C_2-C_8)$alkynylmercapto, $(C_2-C_8)$alkenyloxy, $(C_2-C_8)$alkynyloxy, $(C_3-C_7)$cycloalkyl, $(C_3-C_7)$cycloalkoxy, cyano, mono- and di-$(C_1-C_4$-alkyl)amino, carboxy, $(C_1-C_8)$alkoxycarbonyl, $(C_2-C_8)$alkenyloxycarbonyl, $(C_1-C_8)$alkylmercaptocarbonyl, $(C_2-C_8)$alkynyloxycarbonyl, $(C_1-C_8)$alkylcarbonyl, $(C_2-C_8)$alkenylcarbonyl, $(C_2-C_8)$alkynylcarbonyl, 1-(hydroxyimino)-$(C_1-C_6)$alkyl, 1-$[(C_1-C_4)$alkylimino]-$(C_1-C_4)$alkyl, 1-$[(C_1-C_4)$alkoxyimino]-$(C_1-C_6)$alkyl, $(C_1-C_8)$alkylcarbonylamino, $(C_2-C_8)$alkenylcarbonylamino, $(C_2-C_8)$alkynylcarbonylamino, aminocarbonyl, $(C_1-C_8)$alkylaminocarbonyl, di-$[(C_1-C_6)$alkyl]-aminocarbonyl, $(C_2-C_6)$alkenylaminocarbonyl, $(C_2-C_6)$alkynylaminocarbonyl, $(C_1-C_8)$alkoxycarbonylamino, $(C_1-C_8)$ alkylaminocarbonylamino, $(C_1-C_6)$alkylcarbonyloxy which is unsubstituted or substituted by halogen, nitro, $(C_1-C_4)$alkoxy or phenyl with or without substitution, $(C_2-C_6)$alkenylcarbonyloxy, $(C_2-C_6)$alkynylcarbonyloxy, $(C_1-C_8)$alkylsulfonyl, phenyl, phenyl-$(C_1-C_6)$-alkoxy, phenyl-$(C_1-C_6)$-alkoxycarbonyl, phenoxy, phenoxy-$(C_1-C_6)$-alkoxy, phenoxy-$(C_1-C_6)$-alkoxycarbonyl, phenylcarbonyloxy, phenylcarbonylamino, phenyl-$(C_1-C_6)$-alkylcarbonylamino, where the last 9 radicals are unsubstituted or mono- or polysubstituted, preferably up to trisubstituted, at the phenyl ring by identical or different radicals from the group consisting of halogen, $(C_1-C_4)$alkyl, $(C_1-C_4)$alkoxy, $(C_1-C_4)$haloalkyl, $(C_1-C_4)$haloalkoxy and nitro, and radicals of the formulae —SiR'$_3$, —O—SiR'$_3$, R'$_3$Si—$(C_1-C_8)$-alkoxy, —CO—O—NR'$_2$, —CO—O—N=CR'$_2$, —O—N=CR'$_2$, —N=CR'$_2$, —O—NR'$_2$, —NR'$_2$, —CR"(OR')$_2$ and —O—(CH$_2$)$_m$CR"(OR')$_2$, where the R' in the abovementioned formulae independently of one another are each hydrogen, $(C_1-C_4)$alkyl, phenyl which is unsubstituted or mono- or polysubstituted, preferably up to trisubstituted, by identical or different radicals from the group consisting of halogen, $(C_1-C_4)$alkyl, $(C_1-C_4)$alkoxy, $(C_1-C_4)$haloalkyl, $(C_1-C_4)$haloalkoxy and nitro, or as a pair are a $(C_2-C_6)$alkanediyl chain and m=0 to 6 and R" is hydrogen or $(C_1-C_4)$alkyl, and a substituted alkoxy radical of the formula R$^a$O—CR$^b$R$^c$CR$^d$(OR$^a$)—$(C_1-C_6)$-alkoxy where the R$^a$ independently of one another are each $(C_1-C_4)$alkyl or together straight-chain or branched $(C_1-C_6)$alkanediyl and R$^b$, R$^c$ and R$^d$ independently of one another are each hydrogen or $(C_1-C_4)$alkyl.

Of particular interest are also herbicide/safener combinations according to the invention where in the safeners of the formula (B1) or (B2)

$R^1$ is hydrogen, $(C_1-C_8)$alkyl or $(C_3-C_7)$cycloalkyl where each of the abovementioned carbon-containing radicals is unsubstituted or mono- or polysubstituted by halogen or mono- or disubstituted, preferably monosubstituted, by radicals from the group consisting of hydroxyl, $(C_1-C_4)$alkoxy, carboxy, $(C_1-C_4)$alkoxycarbonyl, $(C_2-C_6)$alkenyloxycarbonyl, $(C_2-C_6)$alkynyloxycarbonyl, 1-(hydroxyimino)-$(C_1-C_4)$alkyl, 1-[$(C_1-C_4)$alkylimino]-$(C_1-C_4)$alkyl, 1-[$(C_1-C_4)$alkoxyimino]-$(C_1-C_4)$alkyl and radicals of the formulae —SiR'$_3$, —O—N=CR'$_2$, —N=CR'$_2$, —NR'$_2$, and —O—NR'$_2$, where the R' in the abovementioned formulae independently of one another are each hydrogen or $(C_1-C_4)$alkyl or as a pair a $(C_4-C_5)$alkanediyl chain, $R^3$ is hydrogen, $(C_1-C_8)$alkyl, $(C_1-C_6)$haloalkyl, $(C_3-C_7)$cycloalkyl or phenyl which is unsubstituted or substituted by one or more radicals from the group consisting of halogen, cyano, nitro, amino, mono- and di-[$(C_1-C_4)$alkyl]amino, $(C_1-C_4)$alkyl, $(C_1-C_4)$haloalkyl, $(C_1-C_4)$alkoxy, $(C_1-C_4)$haloalkoxy, $(C_1C_4)$alkylthio and $(C_1-C_4)$alkylsulfonyl, and $R^4$ is hydrogen, $(C_1-C_8)$alkyl, $(C_1-C_8)$haloalkyl, $(C_1-C_4$-alkoxy)-$(C_1-C_4)$-alkyl, $(C_1-C_6)$hydroxyalkyl, $(C_3-C_7)$cycloalkyl or tri-$(C_1-C_4)$-alkylsilyl, and/or X is hydrogen, halogen, methyl, ethyl, methoxy, ethoxy, $(C_1$ or $C_2)$-haloalkyl, preferably hydrogen, halogen or $(C_1$ or $C_2)$-haloalkyl.

Preference is given to safeners in which in the formula (B1)

X is hydrogen, halogen, nitro or $(C_1-C_4)$haloalkyl, n is 1, 2 or 3 and

Z is a radical of the formula OR$^1$, $R^1$ is hydrogen, $(C_1-C_8)$alkyl or $(C_3-C_7)$cycloalkyl where each of the abovementioned carbon-containing radicals is unsubstituted or mono- or polysubstituted, preferably up to trisubstituted, by identical or different halogen radicals or up to disubstituted, preferably up to monosubstituted, by identical or different radicals from the group consisting of hydroxyl, $(C_1-C_4)$alkoxy, $(C_1-C_4)$alkoxycarbonyl, $(C_2-C_6)$alkenyloxycarbonyl, $(C_2-C_6)$alkynyloxycarbonyl, 1-(hydroxyimino)-$(C_1-C_4)$alkyl, 1-[$(C_1-C_4)$alkylimino]-$(C_1-C_4)$alkyl, 1-[$(C_1-C_4)$alkoxyimino]-$(C_1-C_4)$alkyl and radicals of the formulae —SiR'$_3$, —O—N=R'$_2$, —N=CR'$_2$, —NR'$_2$ and —O—NR'$_2$ where the radicals R' in the abovementioned formulae independently of one another are each hydrogen or $(C_1-C_4)$alkyl or as a pair are $(C_4$ or $C_5)$alkanediyl, $R^3$ is hydrogen, $(C_1-C_8)$alkyl, $(C_1-C_6)$haloalkyl, $(C_3-C_7)$cycloalkyl or phenyl which is unsubstituted or substituted by one or more radicals from the group consisting of halogen, $(C_1-C_4)$alkyl, $(C_1-C_4)$alkoxy, nitro, $(C_1-C_4)$haloalkyl and $(C_1-C_4)$haloalkoxy, and $R^4$ is hydrogen, $(C_1-C_8)$alkyl, $(C_1-C_8)$haloalkyl, $(C_1-C_4)$alkoxy-$(C_1-C_4)$-alkyl, $(C_1-C_6)$hydroxyalkyl, $(C_3-C_7)$cycloalkyl or tri-$(C_1-C_4)$-alkylsilyl.

Preference is also given to safeners in which in the formula (B2)

X is hydrogen, halogen or $(C_1-C_4)$haloalkyl, n is 1, 2 or 3, where $(X)_n$ is preferably 5-Cl, Z is a radical of the formula OR$^1$, R* is CH$_2$ and $R^1$ is hydrogen, $(C_1-C_8)$alkyl, $(C_1-C_8)$haloalkyl or $(C_1-C_4)$alkoxy-$(C_1-C_4)$-alkyl, preferably $(C_1-C_8)$alkyl.

Particular preference is given to safeners in which in the formula (B1)

W is (W1),

X is hydrogen, halogen or $(C_1-C_2)$haloalkyl, n is 1, 2 or 3, where $(X)_n$ is preferably 2,4-Cl$_2$, Z is a radical of the formula OR$^1$, $R^1$ is hydrogen, $(C_1-C_8)$alkyl, $(C_1-C_4)$haloalkyl, $(C_1-C_4)$hydroxyalkyl, $(C_3-C_7)$cycloalkyl, $(C_1-C_4)$alkoxy-$(C_1-C_4)$-alkyl, tri-$(C_1-C_2)$-alkylsilyl, preferably $(C_1-C_4)$alkyl, $R^3$ is hydrogen, $(C_1-C_8)$alkyl, $(C_1-C_4)$haloalkyl or $(C_3-C_7)$cycloalkyl, preferably hydrogen or $(C_1-C_4)$alkyl and $R^4$ is hydrogen, $(C_1-C_8)$alkyl, $(C_1-C_4)$haloalkyl, $(C_1-C_4)$hydroxyalkyl, $(C_3-C_7)$cycloalkyl, $(C_1-C_4)$alkoxy-$(C_1-C_4)$-alkyl or tri-$(C_1-C_2)$-alkylsilyl, preferably hydrogen or $(C_1-C_4)$alkyl.

Particular preference is also given to herbicidal compositions in which in the formula (B1)

W is (W2),

X is hydrogen, halogen or $(C_1-C_2)$haloalkyl, n is 1, 2 or 3, where $(X)_n$ is preferably 2,4-Cl$_2$, Z is a radical of the formula OR$^1$, $R^1$ is hydrogen, $(C_1-C_8)$alkyl, $(C_1-C_4)$haloalkyl, $(C_1-C_4)$hydroxyalkyl, $(C_3-C_7)$cycloalkyl, $(C_1-C_4$-alkoxy)-$C_1-C_4$-alkyl, tri-$(C_1-C_2)$-alkylsilyl, preferably $(C_1-C_4)$alkyl and $R^3$ is hydrogen, $(C_1-C_8)$alkyl, $(C_1-C_4)$haloalkyl, $(C_3-C_7)$cycloalkyl or phenyl, preferably hydrogen or $(C_1-C_4)$alkyl.

Particular preference is also given to safeners in which in the formula (B1)

W is (W3),

X is hydrogen, halogen or $(C_1-C_2)$haloalkyl, n is 1, 2 or 3, where $(X)_n$ is preferably 2,4-Cl$_2$, Z is a radical of the formula OR$^1$, R¹ is hydrogen, $(C_1-C_8)$alkyl, $(C_1-C_4)$haloalkyl, $(C_1-C_4)$ hydroxyalkyl, $(C_3-C_7)$cycloalkyl, $(C_1-C_4)$alkoxy-$(C_1-C_4)$-alkyl, tri-$(C_1-C_2)$-alkylsilyl, preferably $(C_1-C_4)$ alkyl and R⁹ is $(C_1-C_8)$alkyl or $(C_1-C_4)$haloalkyl, preferably $C_1$-haloalkyl.

Particular preference is also given to safeners in which in the formula (B1)

W is (W4),

X is hydrogen, halogen, nitro, $(C_1-C_4)$alkyl or $(C_1-C_2)$ haloalkyl, preferably $CF_3$, or $(C_1-C_4)$alkoxy, n is 1, 2 or 3, m is 0 or 1, Z is a radical of the formula OR¹ and R¹ is hydrogen, $(C_1-C_4)$alkyl, carboxy-$(C_1-C_4)$alkyl or $(C_1-C_4)$alkoxycarbonyl-$(C_1-C_4)$alkyl, preferably $(C_1-C_4)$alkoxy-CO—CH_2$-$, $(C_1-C_4)$alkoxy—CO—C$(CH_3)$H—, HO-CO—CH_2$— or HO—CO—C$(CH_3)$H— and R³ is H, $(C_1-C_4)$alkyl, $(C_1-C_4)$haloalkyl, $(C_3-C_7)$cycloalkyl or phenyl which is unsubstituted or substituted by one or more radicals from the group consisting of halogen, $(C_1-C_4)$alkyl, $(C_1-C_4)$haloalkyl, nitro, cyano and $(C_1C_4)$ alkoxy.

The following groups of compounds are suitable for use as safeners for the abovementioned herbicidally active compounds (A):

a) Compounds of the type of the dichlorophenylpyrazoline-3-carboxylic acid (i.e. the formula (B1) where W=W1 and $(X)_n$=2,4-$Cl_2$), preferably compounds such as mefenpyr-diethyl, i.e. ethyl 1-(2,4-dichlorophenyl)-5-ethoxycarbonyl-5-methyl-2-pyrazoline-3-carboxylate (B1-1) and related compounds as described in WO 91/07874, b) Derivatives of dichlorophenylpyrazolecarboxylic acid (i.e. the formula (B1) where W=W2 and $(X)_n$=2,4-$Cl_2$), preferably compounds such as ethyl 1-(2,4-dichlorophenyl)-5-methylpyrazol-3-carboxylate (B1-2), ethyl 1-(2,4-dichlorophenyl)-5-isopropylpyrazole-3-carboxylate (B1-3), ethyl 1-(2,4-dichlorophenyl)-5-(1,1-dimethylethyl)pyrazole-3-carboxylate (B1-4), ethyl 1-(2,4-dichlorophenyl)-5-phenylpyrazole-3-carboxylate (B1-5) and related compounds as described in EP-A-333 131 and EP-A-269 806.

c) Compounds of the type of the triazolecarboxylic acids (i.e. the formula (B1) where W=W3 and $(X)_n$=2,4-$Cl_2$), preferably compounds such as fenchlorazole-ethyl, i.e. ethyl 1-(2,4-dichlorophenyl)-5-trichloromethyl-(1H)-1,2,4-triazole-3-carboxylate (B1-6) and related compounds (see EP-A-1 74 562 and EP-A-346 620);

d) Compounds of the type of the 5-benzyl- or 5-phenyl-2-isoxazoline-3-carboxylic acid or the 5,5-diphenyl-2-isoxazoline-3-carboxylic acid, preferably compounds such as ethyl 5-(2,4-dichlorobenzyl)-2-isoxazoline-3-carboxylate (B1-7) or ethyl 5-phenyl-2-isoxazoline-3-carboxylate (B1-8) and related compounds as described in WO 91/08202, or ethyl (B1-9) or n-propyl (B1-10) 5,5-diphenyl-2-isoxazoline-carboxylate or ethyl 5-(4-fluorophenyl)-5-phenyl-2-isoxazoline-3-carboxylate (B1-11) as described in the German patent application P 43 31 448.1 (WO-A-95/07897).

e) Compounds of the type of the 8-quinolinoxyacetic acid, for example those of the formula (B2) where $(X)_n$=5-Cl, hydrogen, Z=OR¹, R*=$CH_2$, preferably compounds such as 1-methylhex-1-yl (5-chloro-8-quinolinoxy)acetate (B2-1),
1,3-dimethylbut-1-yl (5-chloro-8-quinolinoxy)acetate (B2-2),
4-allyloxybutyl (5-chloro-8-quinolinoxy)acetate (B2-3),
1-allyloxyprop-2-yl (5-chloro-8-quinolinoxy)acetate (B2-4),
ethyl (5-chloro-8-quinolinoxy)acetate (B2-5),
methyl (5-chloro-8-quinolinoxy)acetate (B2-6),
allyl (5-chloro-8-quinolinoxy)acetate (B2-7),
2-(2-propylideneiminoxy)-1-ethyl (5-chloro-8-quinolinoxy)acetate (B2-8),
2-oxoprop-1-yl (5-chloro-8-quinolinoxy)acetate (B2-9)
and related compounds as described in EP-A-86 750, EP-A-94 349 and EP-A-1 91 736 or EP-A-0 492 366.

f) Compounds of the type of the (5-chloro-8-quinolinoxy) malonic acid, i.e. the formula (B2) where $(X)_n$=5-Cl, Z=OR¹, R*=—CH(COO—alkyl)—, preferably compounds such as diethyl (5-chloro-8-quinolinoxy)malonate (B2-10), diallyl (5-chloro-8-quinolinoxy)malonate (B2-11), methyl ethyl (5-chloro-8-quinolinoxy)malonate (B2-12) and related compounds as described in EP-A-0 582 198.

g) Active compounds of the type of the phenoxyacetic or phenoxypropionic acid derivatives or of the aromatic carboxylic acids such as, for example, 2,4-dichlorophenoxyacetic acid (2,4-D) or salts or esters thereof, 4-chloro-2-methylphenoxypropionic acid (mecoprop), MCPA or salts or esters thereof or 3,6-dichloro-2-methoxybenzoic acid (dicamba) or salts or esters thereof.

The safeners (antidotes) of the formulae (B1) to (B6), for example safeners of the abovementioned groups a) to g), reduce or neutralize phytotoxic effects which can occur when using the herbicidally active compounds (A) in crops of useful plants, without significantly adversely affecting the activity of these herbicidally active compounds against harmful plants. Thus, it is possible to increase the area of use for conventional crop protection agents considerably and to extend it, for example, to crops such as wheat, barley, maize and other Gramineae crops where hitherto use of the herbicides was not possible or possible only with limitations, i.e. at low application rates with a narrow spectrum of activity.

The herbicidally active compounds (A) and said safeners can be applied together (in the form of a finished formulation or by the tank mix method) or in any desired sequence one after the other. In general, differences in the timings of the application should be avoided to ensure a combined action of the two active compounds. The ratio by weight of safener: herbicidal active compound can vary within wide limits and is preferably in the range from 1:100 to 100:1, in particular 1:10 to 10:1. The amounts of herbicidally active compound and safener which are optimal in each case depend on the safener used and on the nature of the plant stand to be treated and can be determined in each individual case by suitable preliminary trials.

The main areas of use for the safeners are in particular maize and cereal crops such as wheat, rye, barley, oats, rice and sorghum, but also cotton and soya beans, preferably cereals and maize.

Depending on their properties, the safeners of the formulae (B1) to (B6) can be used for pretreating the seed of the crop (seed dressing) or are incorporated into the seed furrows before seeding or are used together with the herbicide before or after the plants have emerged. Pre-emergence treatment includes treatment of the area under cultivation before they are seeded as well as treatment of those which have been seeded but where growth has not taken place. Application together with the herbicide is preferred. Tank mixes or finished formulations can be used for this purpose.

The required application rates of safeners can vary within wide limits, depending on the indication and the herbicidally active compound used, and are generally in the range from 0.001 to 5 kg, preferably 0.005 to 0.5 kg, of active compound per hectare.

The present invention therefore also relates to a method of protecting crops against phytotoxic side effects of herbicides (A), which comprises applying an effective amount of a compound of the formulae (B1) to (B6) before, after or together with the herbicidally active compound, to the plants, seeds of plants or the area under cultivation.

The compounds of the formulae (B1) to (B6) and their combinations with the herbicidally active compound can be formulated in various ways, depending on the prevailing biological and/or chemico-physical parameters. The following possibilities are suitable formulations: wettable powders (WP), emulsifiable concentrates (EC), water-soluble powders (SP), water-soluble concentrates (SL), concentrated emulsions (BW), such as oil-inwater and water-in-oil emulsions, sprayable solutions or emulsions, capsule suspensions (CS), oil- or water-based dispersions (SC), suspoemulsions, suspension concentrates, dusts (DP), oil-miscible solutions (OL), seed-dressing products, granules (GR) in the form of microgranules, spray granules, coated granules and adsorption granules, granules for broadcasting and soil application, water-soluble granules (SG), water-dispersible granules (WG), ULV formulations, microcapsules and waxes.

These individual types of formulation are known in principle and are described, for example, in: Winnacker-Küchler, "Chemische Technologie" [Chemical Technology], Volume 7, C. Hauser Verlag Munich, 4th Ed. 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The formulation auxiliaries required, such as inert materials, surfactants, solvents and other additives are also known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., lnterscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th Ed. 1986.

Based on these formulations, it is also possible to prepare combinations with other pesticidally active compounds, such as, for example, insecticides, acaricides, herbicides, fungicides, and also with safeners, fertilizers and/or growth regulators, for example in the form of a ready mix or a tank mix.

Wettable powders are preparations which are uniformly dispersible in water and which, besides the active compound, also comprise ionic and/or nonionic surfactants (wetting agents, dispersants), for example polyethoxylated alkylphenols, polyethoxylated fatty alcohols, polyethoxylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutyinaphthalenesulfonate or else sodium oleoylmethyltaurinate, in addition to a diluent or inert substance. To prepare the wettable powders, the herbicidally active compounds are ground finely, for example in customary equipment such as hammer mills, blower mills and air-jet mills, and simultaneously or subsequently mixed with the formulation auxiliaries.

Emulsifiable concentrates are prepared by dissolving the active compound in an organic solvent, for example butanol, cyclohexanone, dimethylformamide, xylene, or else higher-boiling aromatics or hydrocarbons or mixtures of the organic solvents with the addition of one or more ionic and/or nonionic surfactants (emulsifiers). Examples of emulsifiers which can be used are: calcium salts of alkylarylsulfonic acids such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays such as kaolin, bentonite and pyrophyllite, or diatomaceous earth.

Suspension concentrates can be water- or oil-based. They can be prepared, for example, by wet grinding using commercially available bead mills with an optional addition of surfactants as already mentioned above for example in the case of the other types of formulation.

Emulsions, for example oil-in-water emulsions (EW), can be prepared for example by means of stirrers, colloid mills and/or static mixers using aqueous organic solvents and, if appropriate, surfactants as already mentioned above for example in the case of the other types of formulation.

Granules can be prepared either by spraying the active compound onto adsorptive granulated inert material or by applying active compound concentrates to the surface of carriers such as sand, kaolinites or of granulated inert material by means of binders, for example polyvinyl alcohol, sodium polyacrylate or else mineral oils. Suitable active compounds can also be granulated in the manner which is conventional for the production of fertilizer granules, if desired as a mixture with fertilizers.

Water-dispersible granules are generally prepared by the customary processes such as spray drying, fluidized-bed granulation, disk granulation, mixing with high-speed mixers and extrusion without solid inert material.

For the preparation of disk, fluidized-bed, extruder and spray granules, see, for example, the processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8–57.

For further details on the formulation of crop protection agents see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

Generally, the agrochemical preparations comprise 0.1 to 99% by weight, in particular 0.1 to 95% by weight, of one or more active compounds of the formulae (B1) to (B6) or of the herbicide/antidote mixture (A) and (B1) and/or (B2) and 1 to 99.9% by weight, in particular 5 to 99.8% by weight, of a solid or liquid additive and 0 to 25% by weight, in particular 0.1 to 25% by weight, of a surfactant.

The active compound concentration in wettable powders is, for example, approximately 10 to 90% by weight, the remainder to 100% by weight being composed of customary formulation components. In the case of emulsifiable concentrates, the active compound concentration may amount to approximately 1 to 90, preferably 5 to 80, % by weight. Formulations in the form of dusts comprise 1 to 30% by weight of active compound, in most cases preferably 5 to 20% by weight of active compound, and sprayable solutions comprise approximately 0.05 to 80, preferably 2 to 50, % by weight of active compound. The active compound content of water-dispersible granules depends partly on whether the active compound is in liquid or solid form and on which granulation auxiliaries, fillers and the like are being used. The active compound content of the water-dispersible granules amounts to, for example, between 1 and 95% by weight, preferably between 10 and 80% by weight.

In addition, the abovementioned formulations of active compounds comprise, if appropriate, the adhesives, wetting agents, dispersants, emulsifiers, penetrants, preservatives, antifreeze agents, solvents, fillers, carriers, colorants, antifoams, evaporation inhibitors and pH and viscosity regulators which are customary in each case.

Components which can be used in combination with the active compounds according to the invention in mixed formulations or in the tank mix are, for example, known active compounds as they are described, for example, in Weed Research 26, 441–445 (1986), or "The Pesticide Manual", 10th edition, The British Crop Protection Council and the Royal Soc. of Chemistry, 1994, and the literature cited therein. Examples of active compounds which may be mentioned as herbicides which are known from the literature and which can be combined with the compounds of the formula (I) are the following (note: either the common names in accordance with the International Organization for Standardization (ISO) or the chemical names, if appropriate together with a customary code number, of the compounds are given): acetochlor; acifluorfen; aclonifen; AKH 7088, ie. [[[1-[5-[2-chloro-4-(trifluoromethyl)phenoxy]-2-nitrophenyl]-2-methoxyethylidene]amino]oxy]acetic acid and its methyl ester; alachlor; alloxydim; ametryn; amidosulfuron; amitrol; AMS, ie. ammonium sulfamate; anilofos; asulam; atrazine; azimsulfurone (DPX-A8947); aziprotryn; barban; BAS 516 H, ie. 5-fluoro-2-phenyl4H-3,1-benzoxazin4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafentrole (CH-900); carbetamide; cafentrazone (ICI-A0051); CDAA, ie. 2-chloro-N,N-di-2-propenylacetamide; CDEC, ie. 2-chloroallyl diethyldithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron-ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butyl ester, DEH-1 12); cyperquat; cyprazine; cyprazole; daimuron; 2,4-DB; dalapon; desmedipham; desmetryn; di-allate; dichlobenil; dichlorprop; diclofop and its esters, such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC;

eglinazine-ethyl; EL 77, ie. 5-cyano-1-(1,1-dimethylethyl)-N-methyl-1 H-pyrazole-4arboxamide; endothal; EPTC; esprocarb; ethalfluralin; ethametsulfuron-methyl; ethidimuron; ethiozin; ethofumesate; F5231, ie. N-[2-chloro4-fluoro-5-[4-(3-fluoropropyl)-4,5-dihydro-5-oxo-1H-tetrazol-1-yl]phenyl]ethanesulfonamide; ethoxyfen and its esters (for example ethyl ester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (8482); flumipropyn; flupoxam (KNW-739); fluorodifen; fluoroglycofen-ethyl; flupropacil (UBIC4243); fluridone; flurochloridone; fluroxypyr; flurtamone; fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazamethabenz-methyl; imazapyr; imazaquin and salts, such as the ammonium salt; imazethamethapyr; imazethapyr; imazosulfuron; ioxynil; isocarbamid;

isopropalin; isoproturon; isouron; isoxaben; isoxapyrifop; karbutilate; lactofen; lenacil; linuron; MCPB; mefenacet; mefluidid; metamitron; metazachlor; methabenzthiazuron; metham; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, ie. 6-chloro-N-(3-chloro-2-propenyl)-5-methyl-N-phenyl-3-pyridazinamine; MT 5950, ie. N-[3-chloro-4-(1-methylethyl)phenyl]-2-methylpentanamide; naproanilide; napropamide; naptalam; NC 310, ie. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat;

pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivates, for example quizalofop-ethyl; quizalofop-P4efuryl and -ethyl; renriduron; rimsulfuron (DPX-E 9636); S 275, ie. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, ie. 2-[[7-[2-chloro-4-(trifluoromethyl)phenoxy]-2-naphthalenyl]oxy]propanoic acid and its methyl ester; sulfentrazone (FMC-97285, F-6285); sulfazuron; sulfometuron-methyl; sulfosate (ICI-A0224); sulfosulfuron (MON 37500); TCA; tebutam (GCP-5544); tebuthiuron; terbacil; terbucarb; terbuchlor; terbumeton; terbuthylazine; terbutryn; TFH 450, ie. N,N-diethyl-3-[(2-ethyl-methylphenyl)sulfonyl]-1 H-1,2,4-triazole-1-carboxamide; thenylchlor (NSK-850); thiazafluron; thiazopyr (Mon-1 3200); thidiazimine (SN-24085); thifensulfuron-methyl; thiobencarb; tiocarbazil; tralkoxydim; tri-allate; triasulfuron; triazofenamide; tribenuronmethyl; triclopyr; tridiphane; trietazine; trifluralin; triflusulfuron and esters (for example methyl ester, DPX-66037); trimeturon; tsitodef; vernolate; WL 110547, ie. 5-phenoxy-1-[3-(trifluoromethyl)phenyl]-1H-tetrazole; UBH-509; D489; LS 82-556; KPP-300; NC-324; NC-330; KH-218; DPX—N8189; SC-0774; DOWCO-535; DK-8910; V-53482; PP-600; MBH-001; KIH-9201; ET-751; KIH-6127 and KIH-2023.

For use, the formulations, which are in commercially available form, are, if appropriate, diluted in the customary manner, for example using water in the case of wettable powders, emulsifiable concentrates, dispersions and water-dispersible granules. Preparations in the form of dusts, granules for soil application or for broadcasting and sprayable solutions are conventionally not diluted any further with inert substances prior to use.

The application rate required, of the compounds of the formula (A) according to the invention, varies with the external factors such as, inter alia, temperature, humidity and nature of the herbicide used. It can vary within wide limits, for example between 0.001 and 10.0 kg/ha or more of active substance, but it is preferably between 0.005 and 5 kg/ha.

The following examples serve to illustrate the invention:

A. FORMULATION EXAMPLES a) A dust is obtained by mixing 10 parts by weight of a compound of the formulae (B1) to (B6) or of an active compound mixture of a herbicidally active compound (A) and a safener of the formulae (B1) to (B6) and 90 parts by weight of talc as inert substance and comminuting the mixture in a hammer mill.

b) A wettable powder which is readily dispersible in water is obtained by mixing 25 parts by weight of a compound of the formulae (B1) to (B6) or of an active compound mixture of a herbicidally active compound (A) and a safener of the formulae (B1) to (B6), 64 parts by weight of kaolin-containing quartz as inert substance, 10 parts by weight of potassium lignosulfonate and 1 part by weight of sodium oleoylmethyltaurate as wetting agent and dispersant, and grinding the mixture in a pinned-disk mill.

c) A dispersion concentrate which is readily dispersible in water is obtained by mixing 20 parts by weight of a compound of the formulae (B1) to (B6) or of an active compound mixture of a herbicidally active compound (A) and a safener of the formulae (B1) to (B6), with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.), and grinding the mixture in a ball mill to a fineness of below 5 microns.

d) An emulsifiable concentrate is obtained from 15 parts by weight of a compound of the formulae (B1) to (B6) or of an active compound mixture of a herbicidally active compound (A) and a safener of the formulae (B1) to (B6), 75 parts by weight of cyclohexanone as solvent and 10 parts by weight of oxethylated nonylphenol as emulsifier.

e) Granules which are dispersible in water are obtained by mixing 75 parts by weight of a compound of the formulae (B1) to (B6) or of an active compound mixture of a herbicidally active compound (A) and a safener of the formulae (B1) to (B6), 10" of calcium lignosulfonate, 5" of sodium lauryl sulfate, 3" of polyvinyl alcohol and 7" of kaolin, grinding the mixture on a pinned-disk mill and granulating the powder in a fluidized bed by spraying on water as granulation liquid.

f) Granules which are dispersible in water are also obtained by homogenizing, on a colloid mill, 25 parts by weight of a compound of the formulae (B1) to (B6) or of an active compound mixture of a herbicidally active compound (A) and a safener of the formulae (B1) to (B6), 5" of sodium 2,2'-dinaphthylmethane-6,6'-disulfonate, 2" of sodium oleoylmethyltaurate, 1 part by weight of polyvinyl alcohol, 17 parts by weight of calcium carbonate and 50" of water, precomminuting the mixture, subsequently grinding it on a bead mill and atomizing and drying the resulting suspension in a spray tower by means of a single-substance nozzle.

BIOLOGICAL EXAMPLES

Example 1

In a greenhouse, cereals and various weeds or grasses were grown in pasteboard pots of 9 cm diameter in sandy loam until they had reached a growth stage of 34 leaves, and then treated with the herbicide or the corresponding herbicide/safener combination, using an application rate of 300 l of water/ha.

Four weeks after the treatment, the plants were scored visually for any kind of damage by the active compounds applied, taking into account in particular the extent of lasting adverse effects on growth. The assessment was carried out using a percent scale (0–100%) in comparison to an untreated control.

The results of the experiments show that the safeners according to the invention prevent the phytotoxicity of the herbicides without adversely affecting the herbicidal activity against grasses (see Table 1).

The herbicides can therefore be used in cereals without risk or at a higher dose than would be possible when applied on their own.

TABLE 1

| | | Doses | % damage | | | |
|---|---|---|---|---|---|---|
| Herbicide | Safener | g AS/ha | Wheat | Barley | ALOMY | SETVI |
| A1 | — | 25 | 40 | 35 | 95 | 85 |
| | | 12 | 35 | 25 | 70 | 85 |
| | | 6 | 30 | 25 | 70 | 70 |
| A1 + B1-1 | | 25 + 25 | 10 | 5 | 95 | 90 |
| | | 12 + 12 | 0 | 0 | 80 | 80 |
| | | 6 + 6 | 0 | 0 | 70 | 75 |
| A1 + B1-11 | | 25 + 25 | 15 | 10 | 95 | 85 |
| | | 12 + 12 | 0 | 0 | 85 | 80 |
| | | 6 + 6 | 0 | 0 | 75 | 75 |
| A1 + B2-10 | | 25 + 25 | 10 | 10 | 90 | 90 |
| | | 12 + 12 | 5 | 0 | 90 | 80 |
| | | 6 + 6 | 0 | 0 | 75 | 70 |

Comments:

AS=Active substance (=based on 100% pure active compound)

A1=1-(3-Methoxycarbonyl-6-trifluoromethyl-pyridyl-2-ylsulfonyl)-3-(4,6-dimethoxypyrimidin-2-yl)urea in the form of a water-dispersible powder which was diluted for use with water, B1-1=Ethyl 1-(2,4-dichlorophenyl)-5ethoxycarbonyl-5-methyl-2-pyrazoline-3carboxylate B1-11=Ethyl 5-(4-fluorophenyl)-5-phenyl-2-isoxazoline-3-carboxylate B2-10=Diethyl 2-(5-chloroquinolin-8-oxy)malonate

Example 20

In a field trial under practical conditions, winter barley and winter wheat at a stage of the middle to the end of stocking were in each case treated with the herbicide A1 or the safener B1-1 alone and with the combination of A1 and B1-1. The results of the scoring, which was carried out similarly to Example 1 four weeks after the application, are shown in Table 2.

The safeners according to the invention are found to make possible the use of herbicide without causing any significant damage to the crops and without adversely affecting the herbicidal activity. The application possibilities are significantly improved, in particular, in barley.

TABLE 2

| Herbicide | Safener | Doses g AS/ha | Wheat | Damage in percent Barley | Galium aparine | Stellaria media |
|---|---|---|---|---|---|---|
| A1 | — | 10 | 8 | 47 | 76 | 59 |
|    |    | 20 | 9 | 56 | 80 | 65 |
|    |    | 30 | 9 | 58 | 82 | 73 |
| — | B1-1 | 90 | 0 | 0 | 0 | 0 |
| A1 + | B1-1 | 30 + 90 | 2 | 12 | 92 | 91 |

Comments: see Comments on Table 1 in Example 1. The numbers are mean values of 5 individual experiments. All applications were carried out in April.

What is claimed is:

1. A herbicide/safener combination, which comprises

A) as herbicidally active compound a compound of the formula (A1) or a salt thereof

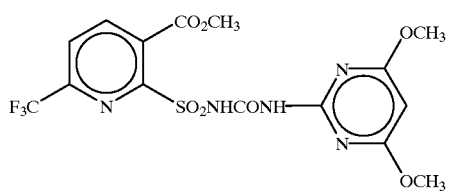

(A1)

and

B) one or more safeners
   a) from the group of the compounds of the formulae (B1) and (B2),

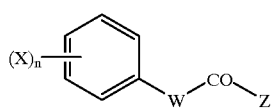

(B1)

-continued

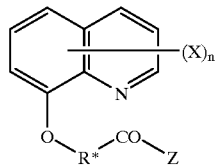

(B2)

in which

X is hydrogen, halogen, $(C_1-C_4)$alkyl, $(C_1-C_4)$alkoxy, nitro or $(C_1-C_4)$haloalkyl, Z is $OR^1$, $SR^1$ or $NR^1R^2$ or is a saturated or unsaturated 3- to 7-membered heterocycle having at least one nitrogen atom and up to 3 hetero atoms which is linked to the carbonyl group in (B1) or (B2) via the nitrogen atom and which is unsubstituted or substituted by radicals from the group consisting of $(C_1-C_4)$alkyl, $(C_1-C_4)$alkoxy or phenyl with or without substitution, R* is a ($C_1$ or $C_2$)-alkanediyl chain which is unsubstituted or substituted by one or two $(C_1-C_4)$alkyl radicals or by $[(C_1-C_3)$-alkoxy]carbonyl, $R^1$ is hydrogen or an unsubstituted or substituted aliphatic hydrocarbon radical, $R^2$ is hydrogen, $(C_1-C_6)$alkyl, $(C_1-C_6)$alkoxy or phenyl with or without substitution, n is an integer from 1 to 5, W is a divalent heterocyclic radical from the group of the partially unsaturated or heteroaromatic five-membered heterocycles having 1 to 3 hetero ring atoms of the type N and O, at least one nitrogen atom and at the most one oxygen atom being present in the ring, or b) from the group of the hormonal growth regulators (auxins) or c) from a combination of the safeners listed under a) and b).

2. The herbicidelsafener combination as claimed in claim 1, which comprises a) a safener of the formula (B1) or (B2), W in the formula (B1) being a radical of the formulae (W1) to (W4),

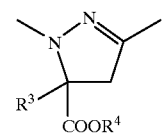

(W1)

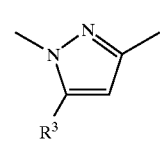

(W2)

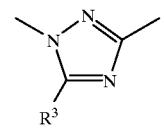

(W3)

(W4)

—(CH$_2$)$_m$—[ring structure with R$^3$, O, N, and CH$_3$]

R$^3$ is hydrogen, (C$_1$–C$_8$)alkyl, (C$_1$–C$_8$)haloalkyl, (C$_3$–C$_{12}$)cycloalkyl or phenyl with or without substitution, R$^4$ is hydrogen, (C$_1$–C$_8$)alkyl, (C$_1$–C$_8$)haloalkyl, (C$_1$–C$_4$)alkoxy(C$_1$–C$_4$)alkyl, (C$_1$–C$_6$)hydroxyalkyl, (C$_3$–C$_{12}$)cycloalkyl or tri-(C$_1$–C$_4$)-alkylsilyl and m is 0 or 1, or b) a safener from the group of the hormonal growth regulators (auxins) of the formulae (B3)–(B6) or salts or esters thereof (B3) [2,4-dichlorophenoxyacetic acid structure]

(B4) [4-chloro-2-methylphenoxyacetic acid structure]

(B5) [chloro methyl phenoxy structure with CH$_3$ branch and CO$_2$H]

(B6) [chlorosalicylic acid methyl ether structure with CO$_2$H, OCH$_3$, Cl]

or c) a combination of the safeners listed under a) and b).

3. The herbicide/safener combination as claimed in claim 2, wherein in the safeners (B1) and (B2)

R$^1$ is hydrogen, (C$_1$–C$_{18}$)alkyl, (C$_3$–C$_{12}$)cycloalkyl, (C$_2$–C$_8$)alkenyl or (C$_2$–C$_8$)alkynyl where the abovementioned carbon-containing radicals are unsubstituted or mono- or polysubstituted by identical or different radicals from the group consisting of halogen, hydroxyl, (C$_1$–C$_8$)alkoxy, (C$_1$–C$_8$)alkylmercapto, (C$_2$–C$_8$)alkenylmercapto, (C$_2$–C$_8$)alkynylmercapto, (C$_2$–C$_8$)alkenyloxy, (C$_2$–C$_8$)alkynyloxy, (C$_3$–C$_7$)cycloalkyl, (C$_3$–C$_7$)cycloalkoxy, cyano, mono- and di-(C$_1$–C$_4$-alkyl)amino, carboxy, (C$_1$–C$_8$)alkoxycarbonyl, (C$_2$–C$_8$)alkenyloxycarbonyl, (C$_1$–C$_8$)alkylmercaptocarbonyl, (C$_2$–C$_8$)alkynyloxycarbonyl, (C$_1$–C$_8$)alkylcarbonyl, (C$_2$–C$_8$)alkenylcarbonyl, (C$_2$–C$_8$)alkynylcarbonyl, 1-(hydroxyimino)-(C$_1$–C$_6$)alkyl, 1-[(C$_1$–C$_4$)alkylimino]-(C$_1$–C$_4$)alkyl, 1-[(C$_1$–C$_4$)alkoxyimino]-(C$_1$–C$_6$)alkyl, (C$_1$–C$_8$)alkylcarbonylamino, (C$_2$–C$_8$)alkenylcarbonylamino, (C$_2$–C$_8$)alkynylcarbonylamino, aminocarbonyl, (C$_1$–C$_8$)alkylaminocarbonyl, di-[(C$_1$–C$_6$)alkyl]-aminocarbonyl, (C$_2$–C$_6$)alkenylaminocarbonyl, (C$_2$–C$_6$)alkynylaminocarbonyl, (C$_1$–C$_8$)alkoxycarbonylamino, (C$_1$–C$_8$)alkylaminocarbonylamino, (C$_1$–C$_6$)alkylcarbonyloxy which is unsubstituted or substituted by halogen, nitro, (C$_1$–C$_4$)alkoxy or phenyl with or without substitution, (C$_2$–C$_6$)alkenylcarbonyloxy, (C$_2$–C$_6$)alkynylcarbonyloxy, (C$_1$–C$_8$)alkylsulfonyl, phenyl, phenyl-(C$_1$–C$_6$)-alkoxy, phenyl-(C$_1$–C$_6$)-alkoxycarbonyl, phenoxy, phenoxy-(C$_1$–C$_6$)-alkoxy, phenoxy-(C$_1$–C$_6$)-alkoxycarbonyl, phenylcarbonyloxy, phenylcarbonylamino, phenyl-(C$_1$–C$_6$)-alkylcarbonylamino, where the last 9 radicals are unsubstituted or mono- or polysubstituted at the phenyl ring by identical or different radicals from the group consisting of halogen, (C$_1$–C$_4$)alkyl, (C$_1$–C$_4$)alkoxy, (C$_1$–C$_4$)haloalkyl, (C$_1$–C$_4$)haloalkoxy and nitro, and radicals of the formulae —SiR'$_3$, —O—SiR'$_3$, R'$_3$Si—(C$_1$–C$_8$)-alkoxy, —CO—O—NR'$_2$, —CO—O—N=CR'$_2$, —O—N=CR'$_2$, —N=CR'$_2$, —O—NR'$_2$, —NR'$_2$, —CR"(OR')$_2$ and —O—(CH$_2$)$_m$CR"(OR')$_2$, where the R' in the abovementioned formulae independently of one another are each hydrogen, (C$_1$–C$_4$)alkyl, phenyl which is unsubstituted or mono- or polysubstituted by identical or different radicals from the group consisting of halogen, (C$_1$–C$_4$)alkyl, (C$_1$–C$_4$)alkoxy, (C$_1$–C$_4$)haloalkyl, (C$_1$–C$_4$)haloalkoxy and nitro, or as a pair are a (C$_2$–C$_6$)alkanediyl chain and m=0 to 6 and R" is hydrogen or (C$_1$–C$_4$)alkyl, and a substituted alkoxy radical of the formula R$^a$O-CR$^b$R$^c$CR$^d$(OR$^a$)-(C$_1$–C$_6$)-alkoxy where the R$^a$ independently of one another are each (C$_1$–C$_4$)alkyl or together straight-chain or branched (C$_1$–C$_6$)alkanediyl and R$^b$, R$^c$ and R$^d$ independently of one another are each hydrogen or (C$_1$–C$_4$) alkyl.

4. The herbicide/safener combination as claimed in claim 2, wherein in the safeners of the formula (B1) or (B2)

R$^1$ is hydrogen, (C$_1$–C$_8$)alkyl or (C$_3$–C$_7$)cycloalkyl where each of the abovementioned carbon-containing radicals is unsubstituted or mono- or polysubstituted by halogen or mono- or disubstituted by radicals from the group consisting of hydroxyl, (C$_1$–C$_4$)alkoxy, carboxy, (C$_1$–C$_4$)alkoxycarbonyl, (C$_2$–C$_6$)alkenyloxycarbonyl, (C$_2$–C$_6$)alkynyloxycarbonyl, 1-(hydroxyimino)-(C$_1$–C$_4$)alkyl, 1-[(C$_1$–C$_4$)alkylimino]-(C$_1$–C$_4$)alkyl, 1-[(C$_1$–C$_4$)alkoxyimino]-(C$_1$–C$_4$)alkyl and radicals of the formulae —SiR'$_3$, —O—N=CR'$_2$, —N=CR'$_2$, —NR'$_2$, and —O—NR'$_2$, where the R' in the abovementioned formulae independently of one another are each hydrogen or (C$_1$–C$_4$)alkyl or as a pair a (C$_4$–C$_5$) alkanediyl chain, R$^3$ is hydrogen, (C$_1$–C$_8$)alkyl, (C$_1$–C$_6$)haloalkyl, (C$_3$–C$_7$) cycloalkyl or phenyl which is unsubstituted or substituted by one or more radicals from the group consisting of halogen, cyano, nitro, amino, mono- and di-[(C$_1$–C$_4$) alkyl]amino, (C$_1$–C$_4$)alkyl, (C$_1$–C$_4$)haloalkyl, (C$_1$–C$_4$) alkoxy, (C$_1$–C$_4$)haloalkoxy, (C$_1$–C$_4$)alkylthio and (C$_1$–C$_4$)alkylsulfonyl, and R$^4$ is hydrogen, (C$_1$–C$_8$)alkyl, (C$_1$–C$_8$)haloalkyl, (C$_1$–C$_4$-alkoxy)-(C$_1$–C$_4$)-alkyl, (C$_1$–C$_6$)hydroxyalkyl, (C$_3$–C$_7$) cycloalkyl or tri-(C$_1$–C$_4$)-alkylsilyl, and/or X is hydrogen, halogen, methyl, ethyl, methoxy, ethoxy, (C$_1$ or C$_2$)-haloalkyl.

5. The herbicide/safener combination as claimed in claim 2, wherein in the safener of the formula (B1)

X is hydrogen, halogen, nitro or (C$_1$–C$_4$)haloalkyl, n is 1, 2 or 3 and

Z is a radical of the formula OR$^1$,

R$^1$ is hydrogen, (C$_1$–C$_8$)alkyl or (C$_3$–C$_7$)cycloalkyl where each of the abovementioned carbon-containing radicals is unsubstituted or mono- or polysubstituted by identical or different halogen radicals or up to disubstituted by identical or different radicals from the group consisting of hydroxyl, $(C_1-C_4)$alkoxy, $(C_1-C_4)$alkoxycarbonyl, $(C_2-C_6)$alkenyloxycarbonyl, $(C_2-C_6)$alkynyloxycarbonyl, 1-(hydroxyimino)-$(C_1-C_4)$alkyl, 1-[$(C_1-C_4)$alkylimino]-$(C_1-C_4)$alkyl, 1-[$(C_1-C_4)$alkoxyimino]-$(C_1-C_4)$alkyl and radicals of the formulae —SiR'$_3$, —O—N=R'$_2$, —N=CR'$_2$, —NR'$_2$ and —O—NR'$_2$ where the radicals R' in the abovementioned formulae independently of one another are each hydrogen or $(C_1-C_4)$alkyl or as a pair are $(C_4$ or $C_5)$alkanediyl, $R^3$ is hydrogen, $(C_1-C_8)$alkyl, $(C_1-C_6)$haloalkyl, $(C_3-C_7)$cycloalkyl or phenyl which is unsubstituted or substituted by one or more radicals from the group consisting of halogen, $(C_1-C_4)$alkyl, $(C_1-C_4)$alkoxy, nitro, $(C_1-C_4)$haloalkyl and $(C_1-C_4)$haloalkoxy, and $R^4$ is hydrogen, $(C_1-C_8)$alkyl, $(C_1-C_8)$haloalkyl, $(C_1-C_4)$alkoxy-$(C_1-C_4)$-alkyl, $(C_1-C_6)$hydroxyalkyl, $(C_3-C_7)$cycloalkyl or tri-$(C_1-C_4)$-alkylsilyl or wherein in the safener of the formula (B2)

X is hydrogen, halogen or $(C_1-C_4)$haloalkyl, n is 1, 2 or 3,

Z is a radical of the formula $OR^1$,

R* is $CH_2$ and $R^1$ is hydrogen, $(C_1-C_8)$alkyl, $(C_1-C_8)$haloalkyl or $(C_1-C_4)$alkoxy-$(C_1-C_4)$-alkyl.

6. The herbicide/safener combination as claimed in claim 2 wherein the safener is of the formula (B1) and W is (W1), X is hydrogen, halogen or $(C_1-C_2)$haloalkyl, n is 1, 2 or 3, Z is a radical of the formula $OR^1$, R' is hydrogen, $(C_1-C_8)$alkyl, $(C_1-C_4)$haloalkyl, $(C_1-C_4)$hydroxyalkyl, $(C_3-C_7)$cycloalkyl, $(C_1-C_4)$alkoxy-$(C_1-C_4)$-alkyl, or tri-$(C_1-C_2)$-alkylsilyl, $R^3$ is hydrogen, $(C_1-C_8)$alkyl, $(C_1-C_4)$haloalkyl or $(C_3-C_7)$cycloalkyl, $R^4$ is hydrogen, $(C_1-C_8)$alkyl, $(C_1-C_4)$ haloalkyl, $(C_1-C_4)$hydroxyalkyl, $(C_3-C_7)$cycloalkyl, $(C_1-C_4)$alkoxy-$(C_1-C_4)$-alkyl or tri-$(C_1-C_2)$-alkylsilyl.

7. The herbicide/safener combination as claimed in claim 2, wherein the safener is of the formula (B1) and W is (W2), X is hydrogen, halogen or $(C_1-C_2)$haloalkyl n is 1, 2 or 3

Z is a radical of the formula OR', $R^1$ is hydrogen, $(C_1-C8)$alkyl, $(C_1-C_4)$haloalkyl, $(C_1-C_4)$hydroxyalkyl, $(C_3-C_7)$cycloalkyl, $(C_1-C_4$-alkoxy)-$C_1-C_4$-alkyl, and tri $(C_1-C_2)$-alkylsilyl, $R^3$ is hydrogen, $(C_1-C_8)$alkyl, $(C_1-C_4)$haloalkyl, $(C_3-C_7)$cycloalkyl or phenyl, preferably hydrogen or $(C_1-C_4)$alkyl.

8. The herbicide/safener combination as claimed in claim 2, wherein the safener is of the formula (B1) and W is (W3), X is hydrogen, halogen or $(C_1-C_2)$haloalkyl, n is 1, 2 or 3 where $(X)_n$, Z is a radical of the formula $OR^1$, $R^1$ is hydrogen, $(C_1-C_8)$alkyl, $(C_1-C_4)$haloalkyl, $(C_1-C_4)$hydroxyalkyl, $(C_3-C_7)$cycloalkyl, $(C_1-C_4)$alkoxy-$(C_1-C_4)$-alkyl, or tri-$(C_1-C_2)$-alkylsilyl, and $R^9$ is $(C_1-C_8)$alkyl or $(C_1-C_4)$haloalkyl.

9. The herbicide/safener combination as claimed in claim 2, where the safener is of the formula B1 and W is (W4), X is hydrogen, halogen, nitro, $(C_1-C_4)$alkyl or $(C_1-C_2)$haloalkyl, n is 1, 2 or 3, m is 0 or 1, Z is a radical of the formula $OR^1$, $R^1$ is hydrogen, $(C_1-C_4)$alkyl, carboxy-$(C_1-C_4)$alkyl or $(C_1-C_4)$alkoxycarbonyl$(C_1-C_4)$alkyl, and $R^3$ is H, $(C_1-C_4)$alkyl, $(C_1-C_4)$haloalkyl, $(C_3-C_7)$cycloalkyl or phenyl which is unsubstituted or substituted by one or more radicals from the group consisting of halogen, $(C_1-C_4)$alkyl, $(C_1-C_4)$haloalkyl, nitro, cyano and $(C_1-C_4)$alkoxy.

10. The herbicide/safener combination according to claim 2, wherein the safener is 2,4-dicholorophenoxyacetic acid.

11. The herbicide/safener combination as claimed in claim 1, wherein the combination is formulated in the form of a preparation (herbicidal composition) and comprises 0.1 to 95% by weight of active compounds (A) and (B) and 1 to 99.9% by weight of customary formulation auxiliaries.

12. The herbicide/safener combination as claimed in claim 1, wherein the combination comprises the active compounds (A) and (B) in a weight ratio of 1:100 to 100:1.

13. The herbicide/safener combination as claimed in claim 1, wherein the safener is of the formula B2 and X is hydrogen, halogen, $(C_1-C_4)$alkyl, $(C_1-C_4)$alkoxy, nitro or $(C_1-C_4)$haloalkyl, n is an integer from 1 to 5, R* is a $(C_1$ or $C_2)$-alkanediyl chain which is substituted by a [$(C_1-C_3)$ -alkoxy]carbonyl group, X is $OR^1$, and $R^1$ is hydrogen or an unsubstituted or substituted $C_1-C_{18}$ hydrocarbon radical.

14. The herbicide/safener combination as claimed in claim 1 wherein the safener is of the formula B2 and X is hydrogen, halogen or $(C_1-C_4)$haloalkyl, n is 1, 2 or 3, Z is a radical of the formula $OR^1$, R* is $CH_2$, and $R^1$ is hydrogen, $(C_1-C_8)$alkyl, $(C_1-C_8)$haloalkyl or $(C_1-C_4)$alkoxy-$(C_1-C_4)$ -alkyl.

15. The herbicide/safener combination according to claim 1, wherein the safener is ethyl 1-(2,4-dichlorophenyl)-5-ethoxycarbonyl-5-methyl-2-pyrazoline 3-carboxylate;

ethyl 5,5-diphenyl-2-isoxazoline-carboxylate;

ethyl 5-(4-flurorophenyl)-5-phenyl-2-isoxazoline-3-carboxylate; or diethyl 2-(5-chloroquinolin-8-oxy) malonate.

16. The herbicide/safener combination according to claim 1, wherein the safener is 1-methylhex-1-yl (5-chloro-8-quinolinoxy) acetate.

17. A method of protecting crops against phytotoxic side effects of herbicides (A), which comprises applying an effective amount of a safener (B) before, after or together with the herbicide (A) to the plants, parts of the plants, seeds of plants or the area under cultivation, the combination of herbicide (A) and safener (B) being defined by claim 1.

* * * * *